(12) United States Patent
Osti et al.

(10) Patent No.: US 6,287,269 B1
(45) Date of Patent: Sep. 11, 2001

(54) DYNAMIC ORTHESIS DEVICE FOR THE CONSERVATIVE TREATMENT OF PATELLOFEMORAL INSTABILITY OF THE KNEE

(76) Inventors: Leonardo Osti, Via Cernazai, 7/A, 33100 Udine; Luciano Saveri, Via Leonardo da Vinci, 22, 40033 Casalecchio di Reno, both of (IT)

( * ) Notice: Subject to any disclaimer, the term of this patent is extended or adjusted under 35 U.S.C. 154(b) by 0 days.

(21) Appl. No.: 09/293,977

(22) Filed: Apr. 19, 1999

(30) Foreign Application Priority Data

Apr. 20, 1998 (IT) .............................................. FE980006 U

(51) Int. Cl.⁷ ...................................................... A61F 13/00
(52) U.S. Cl. .................................. 602/62; 602/61; 602/63
(58) Field of Search .................................. 602/5, 20, 23, 602/26, 60, 61, 62, 63; 2/455, 24; 128/892

(56) References Cited

U.S. PATENT DOCUMENTS

| | | | |
|---|---|---|---|
| 4,296,744 | * 10/1981 | Palumbo ................................ | 602/62 |
| 4,532,921 | * 8/1985 | Von Torklus et al. ................... | 602/62 |
| 5,139,015 | * 8/1992 | Morneau ................................ | 602/62 |
| 5,417,646 | * 5/1995 | Gauvry ................................... | 602/26 |
| 5,417,647 | * 5/1995 | Down ..................................... | 602/26 |
| 5,613,943 | * 3/1997 | Palumbo ................................ | 602/62 |
| 5,695,452 | * 12/1997 | Grim et al. ............................... | 602/6 |
| 5,800,491 | * 9/1998 | Kolen et al. ........................... | 607/108 |
| 5,807,298 | * 9/1998 | Palumbo .................................. | 602/62 |

OTHER PUBLICATIONS

Smith and Nephew Donjoy, Donjoy Products Catalog, pp. 48–49, 1994.*

* cited by examiner

Primary Examiner—Kim M. Lee
(74) Attorney, Agent, or Firm—Guido Modiano; Albert Josif; Daniel O'Byrne

(57) ABSTRACT

A structural element having a crescent-shaped side support with a D-shaped cross-section and a hemisphere at its ends; its sloping-edge shape and the visco-elastic material of which it is made allow it, once it has been arranged laterally to the patella and subjected to adequate medial traction, to adapt to the anatomical shape of the patella. Two belts of inelastic material are structurally integrated with the support at its ends and can be orientated through an arc of 45°, allowing to apply a direct and adjustable traction to the support, thus producing medializing forces on the patella which is functional to correct the different patterns of patellar instability. In order to keep the orthesis in place whilst it is being worn and avoid the loss of alignment with the patella during use, a strip of viscous material has been applied to the upper edge of the internal wall of the invention; the material, when rested on the skin, has a non-slip effect even with intense perspiration.

20 Claims, 3 Drawing Sheets

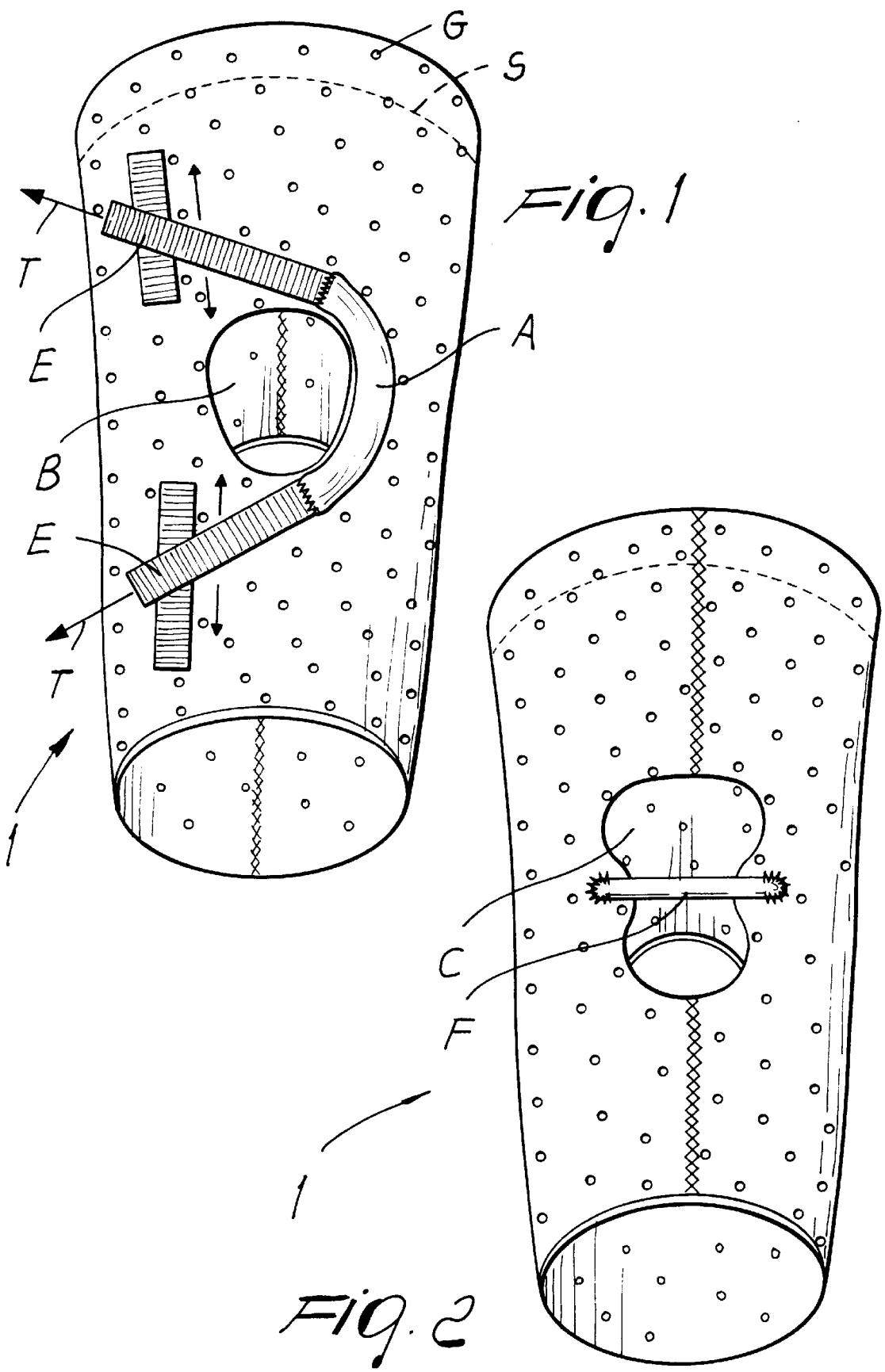

DYNAMIC ORTHESIS DEVICE FOR THE CONSERVATIVE TREATMENT OF PATELLOFEMORAL INSTABILITY OF THE KNEE

BACKGROUND OF THE INVENTION

The orthesis device according to the invention is specifically designed for the conservative treatment of patellofemoral instability of the knee.

Patellar instability is in fact characterized by a gradual loss of patellofemoral articular alignment, with gradual lateral displacement of the patellar position with respect to the position of the femoral trochlea, which can be classified, depending on the severity of the condition, as follows:

(i) external patellar hyperpressure (the patellar tangential axis is dislocated outward with respect to the axis of the femoral trochlea);

(ii) patellar subluxation (partial loss of articular relationships); and (iii) full luxation (with complete loss of articular relationships and consequent absolute functional disability).

The cause of the disorder can be found in static alterations, such as a decrease in patellar dysplasia and condylar displasia convexity and/or in the concavity of the femoral trochlea, and in dynamic ones, such as alterations to trophic conditions and to the insertion (lever arm) of the muscles that have a medializing action. The altered patellofemoral alignment is accompanied by an imbalance in the distribution of articular loads, with early wear of the cartilage (covering of the joint surfaces) and becomes clinically manifest with symptoms such as pain, effusions and articulation failures (patellar pseudoseizures). The condition reaches its peak in patellar luxations, where complete loss of articular relationships causes the functional locking of the articulation.

Indications for treatment, defined in relation to an extensive review of the literature, entail:

(1) surgical treatment, electively recommended for recurrent luxations and for minor instabilities which show symptoms despite conservative treatment; and (2) conservative treatment, including physical therapy, elective strengthening of muscles having a medializing action and stretching of the posterior muscles of the thigh and of the lateral capsular and tendon structures, associated with the use of ortheses.

Conservative treatment can therefore include the use of patellar stabilization ortheses, all of which have the common purpose of restoring normal articular alignment by acting with various methods:

1) patellar centering hole;

2) stabilization system with crossing bands centered on the patella;

3) stabilization system using bands which produce a medializing pressure using traction belts or a presser support.

The drawbacks shown by the ortheses produced so far can be summarized as follows:

1) insufficient medializing action, which fails to produce sufficient alignment of the patellofemoral articulation through flexing and extension;

2) low compliance and limitation of the articulation;

3) pressure due to tangential action which induces an excessive articular load and sustains the associated synovial-capsular inflammation;

4) excessive compressive forces induced on the soft tissues of the posterior region of the knee (muscle and tendon insertions and vascular-nerve structures running in the popliteal area).

The above shortcomings become clinically manifest as:

1) failed reduction of "patellar snapping" occurring on flexing and extension of the knee and produced by contact of the patellar surface with the external "side" surface of the trochlea;

2) difficulty in maintaining an adequate ratio between alignment of the orthesis and the possibility to obtain functional range of motion of the joint for everyday and sports activity of the femur;

3) increase in anterior knee pain, particularly evident in the case of activities which entail marked flexing of the knee;

4) compressive action, which can cause the latency and aggravation of vascular or muscle and tendon disorders in the posterior region of the knee and of the popliteal canal.

SUMMARY OF THE INVENTION

The design of the orthesis hereinafter described arises, therefore, from a biomechanical and functional analysis of currently produced orthesis models and proposes a conceptual and substantial improvement obviating the described limitations.

The conceptual and structural improvements that have been applied can be summarized as follows:

I) The provision of an anatomical pressure support which can be customized as for the traction direction (T). At this level, the improvement introduced can be divided into three elements:

1) the shape of the lateral patellar containment supporting element or support (A), which reflects the anatomical shape of the patella and has a sloping contact surface which is effective in limiting, during continuous contact, the stimulation and irritation of the peripatellar synovial tissue that is often observed;

2) the presence of two traction belts or arms (E), which are directly connected to the support and integrated therein so as to allow the correct and most effective transmission of patellofemoral medializing/aligning forces;

3) the possibility to direct the traction forces (T) of the belts (E) with a particular possibility of selectable angular orientation through an angle of approximately 45°, so as to allow customized adjustment of the corrective forces that medialize and align the patellofemoral articulation also in relation to other variables, such as for example the different height of the patella with respect to the center of the femoral trochlea (high patella or low patella).

II) An anatomical centering hole (B), which by reproducing the true shape of the patella reduces tangential compression forces.

III) A butterfly-shaped anatomical posterior opening (C), which eliminates compressive forces acting on the soft tissues of the posterior region of the knee. The posterior opening does not compromise structural integrity because it is integrated with an elastic stabilization bar band (F), which is required in order to maintain the structural stability of the orthesis and alignment whilst the orthesis is being worn.

IV) An anchoring system in order to avoid the brace slipping during sports activity (entire knee brace-patellar support).

V) Ventilation holes (G) in order to improve compliance, reducing overheating and skin perspiration.

This model of orthesis for the conservative treatment of patellofemoral instability, by virtue of the particular patellar centering system, allows to modulate and customize, according to the degree of the disorder, the traction/pressure forces required to improve the patellofemoral articular alignment in static conditions and the proper function of the joint during activities.

BRIEF DESCRIPTION OF THE DRAWINGS

Further characteristics and advantages of the present invention will become apparent from the following description of a preferred embodiment, illustrated only by way of non-limitative example in the accompanying drawings, wherein:

FIG. 1 is a front view of a left knee brace;

FIG. 2 is a rear view of the knee brace;

DESCRIPTION OF THE PREFERRED EMBODIMENTS

Figure 3:
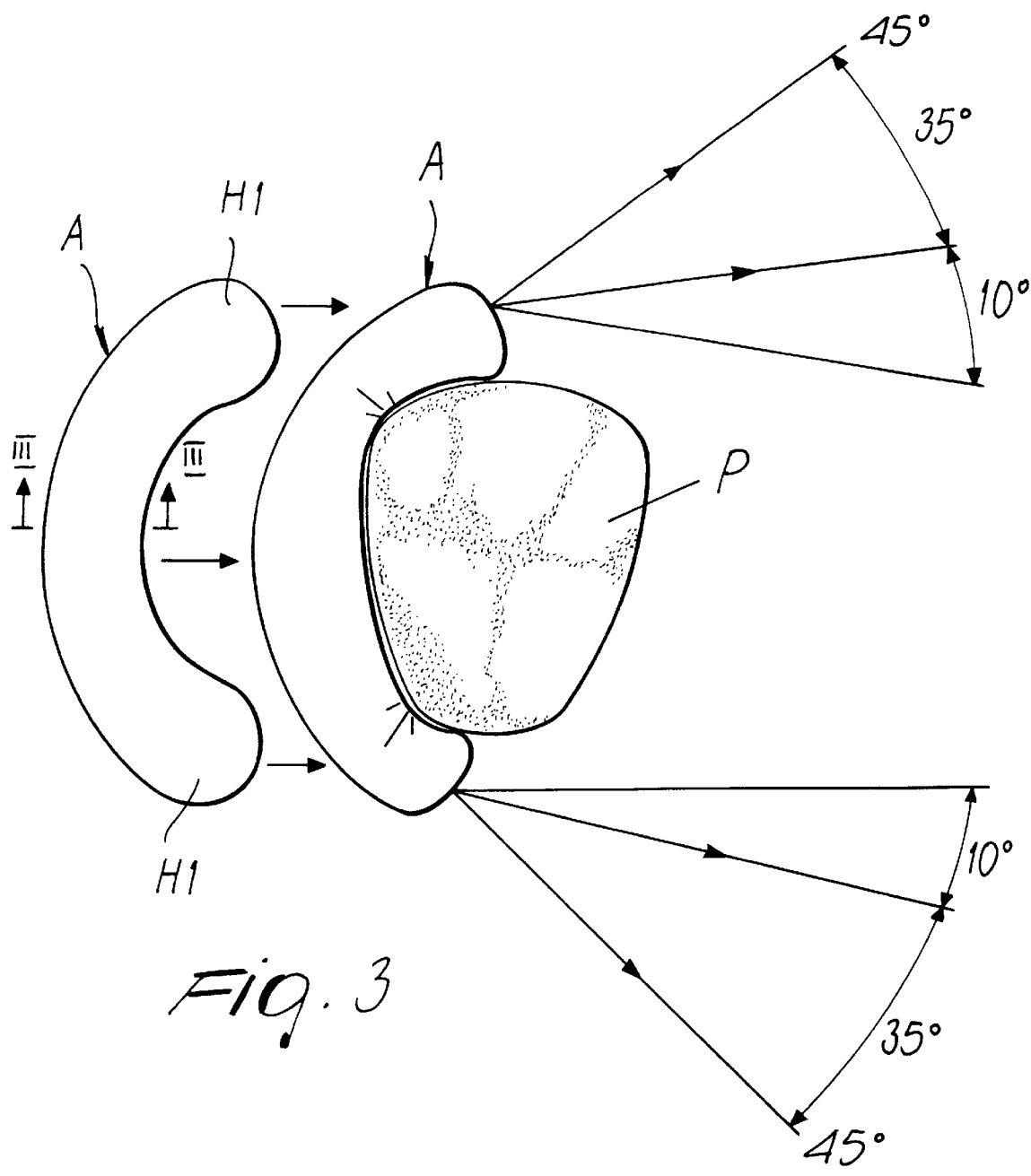
FIG. 3 is a view of the patellar centering system and of the traction/pressure forces.
Figure 3A:
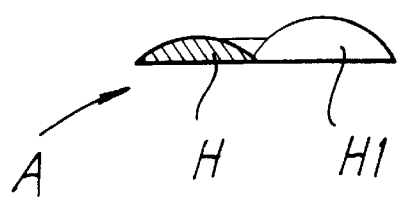
FIG. 3A is a cross-sectional view, taken along the line III—III of FIG. 3.

With reference to the above figures, the orthesis device is constituted by a knee brace is generally designated by the reference numeral 1.

The device according to the invention is constituted by an integrated tubular structure made of visco-elastic material, with dermocompatible characteristics which has two openings: a first anterior oval hole, constituting the anatomical centering hole (B), adapted to anatomically adapt to the configuration of the patella, and a second butterfly-shaped hole (C), in order to eliminate or reduce to minimal levels the stresses that act on the muscle, tendon, vascular and nerve structures of the posterior area of the knee.

Said hole (C) is divided horizontally approximately in half by a band (F) made of the same material as the device according to the invention, which by connecting the two ends of the hole (C) allows it to maintain the correct tension on the knee while maintaining the popliteal region free during flexing.

A particular structural feature of the invention is constituted by the crescent-shaped side supporting element or support (A), which has a D-shaped cross-section (H) with half-sphere shaped ends (H1); its sloping-edge cross-sectional shape and its visco-elastic material (preferably silicone, neoprene and a combination of synthetic fibers and filaments known under the trademark Lycra) allow, when the element (A) is arranged laterally to the patella (P) and is subjected to adequate medial traction, as shown by the arrows of FIG. 3, to adapt to the anatomical shape of said patella.

Two belts or arms (E) are structurally integrated with said support (A) at ends thereof; said belts or arms are made of inelastic material and can be orientated over an arc of approximately 45°, allowing to apply direct and adjustable traction forces (T) on the support (A), thus producing a variable medializing pressure on the patella (P) (FIG. 3) in order to correct the different pattern of patellar height and rotational deformity.

In order to keep the orthesis in position while it is being worn and avoid slippage during use, in the upper edge of the internal wall of the device according to the invention, an anchoring system constituted by a strip (S) of viscous materials is provided which, when rested against the skin, has a non-slip effect even in case of intense perspiration.

The operation of the device is readily apparent from the description above and from the figures.

Figure 4:
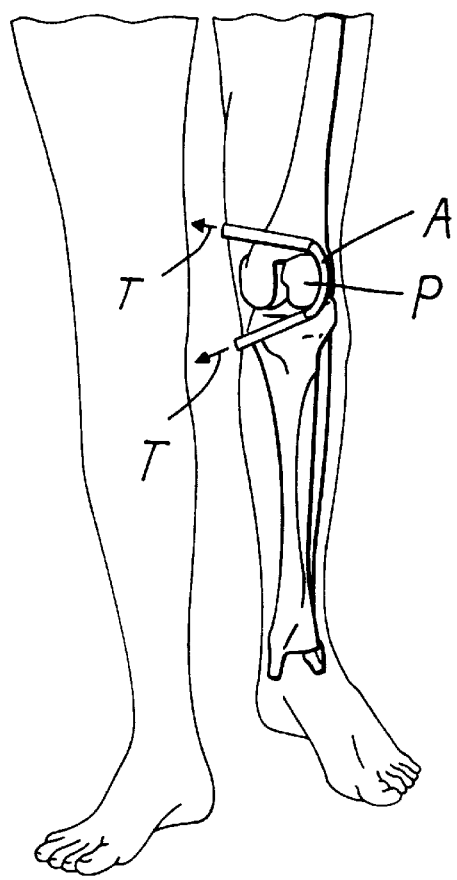
FIG. 4 is a schematic representation of the supporting element while acting on a knee patella.

In particular, in FIG. 4, it is shown schematically the function mode of the device, with the pad, i.e. the supporting element A in active position, during the treatment.

Figure 6:
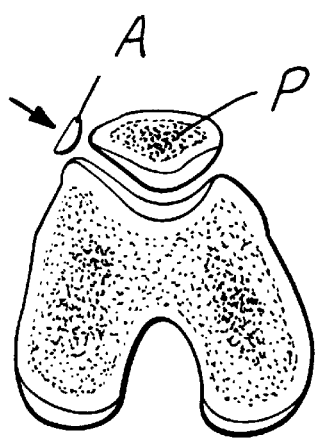
FIG. 6 is a cross-sectional front view of a knee joint with the supporting element applied.
Figure 7:
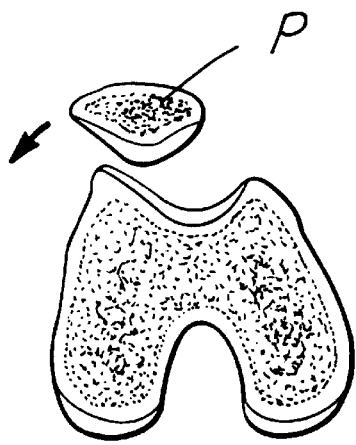
FIG. 7 is a cross-sectional front view of a knee joint with shown a lateral displacement of the patella position.

The traction forces exerted through the two belts (E), while adapting the pad A around the side of the patella, have the effect of pushing the same patella as shown in the cross-sectional view of FIG. 6. A correction of a displacement of the type shown in FIG. 7 is thus possible.

Figure 5:
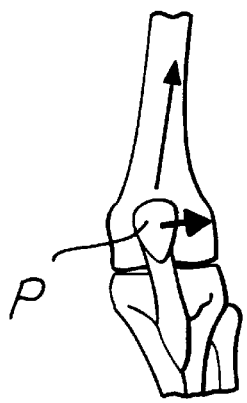
FIG. 5 is a partial, schematic view of a knee joint on which a lateral-medial traction force, as exerted by the device, is shown.

The traction forces (T) exerted on the two belts (E) of the device according to the invention, generate a lateral-medial force, as exemplified in FIG. 5.

The disclosures in Italian Utility Application No. FE98U000006 from which this application claims priority are incorporated herein by reference.

What is claimed is:

1. An orthesis device for the conservative treatment of patellofemoral instability of a knee, comprising:

a supporting element with a D-shaped cross-section adapted to contain laterally a knee patella, said supporting element having a half-moon configuration with hemispherical ends and being customizable to adapt to any patella configuration according to a traction direction towards the patella; and traction arms, made of an inelastic material, and connected to said supporting element to apply direct traction forces with selectable angular orientations with respect to a horizontal direction so as to generate an adjustable resultant traction on the knee patella along said traction direction.

2. The device of claim 1, wherein said supporting element has a sloping tissue contact surface shaped so as to adapt to different anatomical patella configurations, said tissue contact surface limiting, during continuous contact, stimulation and irritation of a peripatellar synovial tissue.

3. The device of claim 1, wherein said traction arms are constituted by two traction belts, which are directly connected to said supporting element and integrated therewith, said traction belts being actuatable through said traction forces to allow correct and effective transmission of patellar medializing and aligning forces.

4. The device of claim 3, wherein said angular orientations of the traction forces exerted on said traction belts are selectively set by placing said traction belts at angles, with respect to the horizontal direction, which are in a range of up to 45°, whereby to provide a customized adjustment of a medial pressure applied by said supporting element on the knee patella for different heights of the patella with respect to a center of the femoral trochlea, and for rotational deformities of the lower limb axis.

5. The device of claim 4, further comprising a tubular knee-structure, applicable in a knee area of a leg of a person, and including a first anterior hole constituting an anatomical centering hole for said tubular knee-structure, said first anterior hole being adapted to anatomically adapt to the different configurations of the knee patella, and said supporting element being arranged laterally to said first anterior hole.

6. An orthesis device for conservative treatment of a patellofemoral instability of a knee, comprising
   a tubular knee-brace structure, applicable in a knee area of a leg of a person;
   a first anterior hole, located in said tubular knee-brace structure for anatomically adapting to a configuration of a patella of the knee;
   a second posterior hole, located in said tubular knee-brace structure, for eliminating compressive forces acting on any of soft tissues, muscles, tendons, vascular and nerve structures located at a popliteal region of the knee; and
   a stabilization band provided at said second posterior hole so as to connect opposite perimetral regions thereof for maintaining appropriate tension on the knee while keeping free, during leg flexing, the popliteal region.

7. The device of claim 6, wherein said knee-brace structure is made of a visco-elastic material with dermocompatible characteristics.

8. The device of claim 6, wherein said stabilization band is made of a visco-elastic material with dermocompatible characteristics so as to maintain structural stability of the tubular knee-brace structure and alignment thereof during use.

9. The device of claim 6, further comprising a patellar centering system for modulating and customizing, according to any particular degree of instability, traction and pressure forces required to achieve proper patellofemoral joint alignment in static and dynamic conditions and a correct operation thereof.

10. The device of claim 9, wherein said patellar centering system comprises a supporting element with a D-shaped cross-section for containing laterally the knee patella, said supporting element having a half-moon configuration with hemispherical ends and being customizable to correct any patellar instability pattern for any patella configuration, according to a traction direction towards said patella.

11. The device of claim 10, wherein said patellar centering system further comprises two traction belts which are directly connected to said supporting element and integrated therewith, said traction belts being actuatable by traction forces to allow correct and effective transmission of patellar medializing and aligning forces.

12. The device of claim 11, wherein said traction belts are actuatable by traction forces having an angular orientation in a range of up to 45°, so as to allow customized adjustment of a medial pressure exerted by said supporting element for different heights of the patella with respect to a center of the femoral trochlea.

13. The device of claim 6, wherein said tubular knee-brace structure and said stabilization band are made of a visco-elastic material with dermocompatible characteristics comprising a combination of silicone, neoprene and synthetic fibers and filaments.

14. The device of claim 6, further comprising a strip of viscous material with a non-slip effect located at an upper and inner border area of the tubular knee-brace structure.

15. An orthesis device for the conservative treatment of patellofemoral instability of a knee, comprising a supporting element with a D-shaped cross-section adapted to contain laterally a knee patella and having a half-moon configuration with hemispherical ends and a sloping tissue contact surface, said contact surface limiting, during continuous contact, stimulation and irritation of a peripatellar synovial tissue, said supporting element being further customizable to adapt to different anatomical configurations of the patella according to a traction direction towards the patella.

16. The device of claim 15, comprising two traction belts which are directly connected to said supporting element and integrated therewith, said traction belts being actuatable by traction forces to allow correct and effective transmission of patellar medializing and aligning forces.

17. The device of claim 16, wherein said belts are actuatable by traction forces having an angular orientation in a range of up to 45°, so as to allow customized adjustment of medial pressure of said supporting element for different heights of the patella with respect to a center of the femoral trochlea, and for rotational deformities of the lower limb axis.

18. The device of claim 17, further comprising:
   a tubular knee-brace structure, applicable in a knee area of a leg of a person;
   a first anterior hole, located in said tubular structure for anatomically adapt to the configuration of the knee patella, said supporting element being arranged laterally to said first anterior hole;
   a second posterior hole, located in said tubular structure, for eliminating compressive forces acting on any of soft tissues, muscles, tendons, vascular and nerve structures located at a popliteal region of the knee; and
   a stabilization band provided at said second posterior hole so as to connect opposite perimetral regions thereof for maintaining appropriate tension on the knee while keeping free during leg flexing the popliteal region.

19. The device of claim 18, wherein said knee-brace structure is made of a visco-elastic material with dermocompatible characteristics.

20. The device of claim 18, wherein said stabilization band is made of a visco-elastic material with dermocompatible characteristics so as to maintain structural stability of the brace and alignment thereof during use.

* * * * *